United States Patent
Garcia Molina et al.

(10) Patent No.: US 10,183,142 B2
(45) Date of Patent: Jan. 22, 2019

(54) SYSTEM AND METHOD FOR ENHANCING SLEEP SLOW WAVE ACTIVITY BASED ON CARDIAC ACTIVITY

(71) Applicant: KONINKLIJKE PHILIPS N.V., Eindhoven (NL)

(72) Inventors: Gary Nelson Garcia Molina, Madison, WI (US); Cristian Nicolae Presura, Veldhoven (NL); Stefan Pfundtner, Eindhoven (NL); Sander Theodoor Pastoor, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 538 days.

(21) Appl. No.: 14/783,114

(22) PCT Filed: Apr. 1, 2014

(86) PCT No.: PCT/IB2014/060338
§ 371 (c)(1),
(2) Date: Oct. 13, 2015

(87) PCT Pub. No.: WO2014/167457
PCT Pub. Date: Oct. 16, 2014

(65) Prior Publication Data
US 2016/0045706 A1 Feb. 18, 2016

Related U.S. Application Data

(60) Provisional application No. 61/810,289, filed on Apr. 10, 2013.

(51) Int. Cl.
*A61M 21/02* (2006.01)
*A61B 5/00* (2006.01)
*A61B 5/024* (2006.01)

(52) U.S. Cl.
CPC ......... *A61M 21/02* (2013.01); *A61B 5/02416* (2013.01); *A61B 5/486* (2013.01);
(Continued)

(58) Field of Classification Search
CPC ............ A61M 21/02; A61M 2210/086; A61M 2210/04; A61M 2205/50;
(Continued)

(56) References Cited

U.S. PATENT DOCUMENTS

2006/0106275 A1  5/2006  Raniere
2008/0234785 A1  9/2008  Nakayama et al.
(Continued)

FOREIGN PATENT DOCUMENTS

JP  2001099463 A  4/2001
JP  2007050144 A  3/2007

OTHER PUBLICATIONS

Poh et al, "Non-Contact, Automated Cardiac Pulse Measurements Using Video Imaging and Blind Source Separation", Optics Express, vol. 18, No. 10, May 10, 2010, p. 10762.
(Continued)

*Primary Examiner* — Kaylee Wilson (57) ABSTRACT

The present disclosure pertains to a system and method for managing a sleep session of a subject. Managing the sleep session is based on cardiac activity in the subject during the sleep session. Cardiac activity, as monitored via one or more sensors worn on an extremity of the subject and/or placed at a distance from the subject, is used to determine periods of slow wave sleep. Sensory stimulation is delivered to the subject during the periods of slow wave sleep to enhance slow wave activity. Wearing a sensor on an extremity, and/or placing a sensor at a distance from the subject during sleep, as opposed to the subject wearing an EEG cap, is more comfortable for the subject.

15 Claims, 6 Drawing Sheets

(52) U.S. Cl.
CPC .......... *A61B 5/4812* (2013.01); *A61B 5/4815* (2013.01); *A61B 5/6824* (2013.01); *A61B 5/6826* (2013.01); *A61B 5/6828* (2013.01); *A61B 5/6829* (2013.01); *A61M 2205/3303* (2013.01); *A61M 2205/3306* (2013.01); *A61M 2205/50* (2013.01); *A61M 2210/04* (2013.01); *A61M 2210/083* (2013.01); *A61M 2210/086* (2013.01); *A61M 2230/005* (2013.01); *A61M 2230/04* (2013.01); *A61M 2230/06* (2013.01); *A61M 2230/10* (2013.01)

(58) Field of Classification Search
CPC .... A61M 2205/3303; A61M 2210/083; A61M 2230/005; A61M 2230/04; A61M 2230/06; A61B 5/02416; A61B 5/4815; A61B 5/486; A61B 5/4812
See application file for complete search history.

(56) References Cited

U.S. PATENT DOCUMENTS

| | | |
|---|---|---|
| 2010/0081943 A1 | 4/2010 | Watson et al. |
| 2011/0021866 A1 | 1/2011 | Iizuka et al. |
| 2012/0251989 A1 | 10/2012 | Wetmore et al. |

OTHER PUBLICATIONS

Verkruysse et al, "Remote Plethysmographic Imaging Using Ambient Light. References and Links", Optics Express, Dec. 12, 2008, p. 21434-21445.

Hori et al, "Proposed Supplements and Amendments to 'A Manual of Standardized Terminology, Techniques and Scoring System for Sleep Stages of Human Subjects', The Rechtschaffen & Kales (1968) Standard", Psychiatry and Clinical Neurosciences, Blackwell Science, Vol. 55, No. 3, Jun. 1, 2001.

Busek et al, "Spectral Analysis of Heart Rate Variability in Slee", Physiol. Res., vol. 54, 2005, p. 369-376.

Tononi, "Enhancing Sleep Slow Waves With Natural Stimuli", Medicamundi, vol. 54, No. 2, 2010, p. 82-88.

Nitzan et al, "Very Low Frequency Variability in Arterial Blood Pressure and Blood Volume Pulse", Med. Biol. Eng. Comput., vol. 37, 1999, p. 54-58.

Tononi, Sleep Function and Synaptic Homeostasis, Sleep Medicine Reviews, vol. 10, 2006, p. 49-62.

Massimini et al, "Triggering Sleep Slow Waves by Transcranial Magnetic Stimulation", PNAS, vol. 104, No. 20, May 15, 2007, p. 8496-8501.

Colrain, "The K-Complex: A 7-Decade History", Sleep, vol. 28, No. 2, Feb. 2005, p. 255-273.

SYSTEM AND METHOD FOR ENHANCING SLEEP SLOW WAVE ACTIVITY BASED ON CARDIAC ACTIVITY

CROSS-REFERENCE TO PRIOR APPLICATIONS

This application is the U.S. National Phase application under 35 U.S.C. § 371 of International Application Serial No. PCT/IB2014/060338, filed on Apr. 1, 2014, which claims the benefit of U.S. Application Ser. No. 61/810,289, filed on Apr. 10, 2013. These applications are hereby incorporated by reference herein.

BACKGROUND

1. Field

The present disclosure pertains to a system and method for managing a current sleep session of a subject based on output signals generated by one or more sensors that convey information related to a pulse rate and/or a blood volume of the subject during the current sleep session.

2. Description of the Related Art

Systems for monitoring sleep are known. Typical systems for monitoring sleep include an electroencephalogram (EEG) cap worn on the head of a user during sleep. The EEG cap decreases the comfort level of the user which may interrupt sleep. Sensory stimulation during sleep is known. Sensory stimulation during sleep is often applied continuously and/or at intervals that do not correspond to sleeping patterns of a subject. The present disclosure overcomes deficiencies in prior art systems.

SUMMARY

Accordingly, one or more aspects of the present disclosure relate to a system configured to manage a current sleep session of a subject. The system comprises one or more sensory stimulators, one or more sensors, and one or more processors. The one or more sensory stimulators are configured to provide sensory stimuli to the subject. The one or more sensors are configured to generate output signals conveying information related to one or more of a pulse rate or a blood volume of the subject during the current sleep session. The one or more processors are configured to execute computer program modules. The computer program modules comprise a parameter module, a sleep stage module, and a control module. The parameter module is configured to determine one or more cardiac activity parameters based on the output signals. The one or more cardiac activity parameters include one or more of a pulse rate metric or a blood volume metric. The pulse rate metric and the blood volume metric are related to a current sleep stage of the subject during the current sleep session. The sleep stage module is configured to determine the current sleep stage of the subject based on the determined parameters. The sleep stage module is configured to determine whether the subject is presently in slow wave sleep. The control module is configured to control the one or more sensory stimulators to provide the sensory stimuli to the subject to enhance slow wave activity (SWA) in the subject while the subject is determined to be in slow wave sleep. In some embodiments, SWA may be estimated by way of an electroencephalogram (EEG). In some embodiments, SWA corresponds to the power of the EEG signal in the 0.5-4.0 Hz band.

Yet another aspect of the present disclosure relates to a method for managing a current sleep session of a subject with a management system. The system comprises one or more sensory stimulators, one or more sensors, and one or more processors configured to execute computer program modules. The computer program modules comprise a parameter module, a sleep stage module, and a control module. The method comprises generating output signals conveying information related to one or more of a pulse rate or a blood volume of the subject during the current sleep session with the one or more sensors; determining, with the parameter module, one or more cardiac activity parameters based on the output signals, the one or more cardiac activity parameters including one or more of a pulse rate metric or a blood volume metric, the pulse rate metric and the blood volume metric being related to a current sleep stage of the subject during the current sleep session; determining, with the sleep stage module, the current sleep stage of the subject based on the determined parameters; determining, with the sleep stage module, whether the subject is presently in slow wave sleep; and controlling, with the control module, the one or more sensory stimulators to provide sensory stimuli to the subject to enhance slow wave activity in the subject while the subject is determined to be in slow wave sleep. In some embodiments, the one or more sensory stimulators are controlled to provide sensory stimuli to the subject to induce sleep slow waves. The manifestation of induced sleep slow waves may be measured via slow wave activity.

Still another aspect of present disclosure relates to a system configured to manage a current sleep session of a subject. The system comprises means for providing sensory stimuli to the subject; means for generating output signals conveying information related to one or more of a pulse rate or a blood volume of the subject during the current sleep session; and means for executing computer program modules. The computer program modules comprise means for determining one or more cardiac activity parameters based on the output signals, the one or more cardiac activity parameters including one or more of a pulse rate metric or a blood volume metric, the pulse rate metric and the blood volume metric being related to a current sleep stage of the subject during the current sleep session; means for determining the current sleep stage of the subject based on the determined parameters, the means for determining the current sleep stage configured to determine whether the subject is presently in slow wave sleep; and means for controlling the means for providing sensory stimuli to provide the sensory stimuli to the subject to enhance the slow wave activity in the subject while the subject is determined to be in slow wave sleep.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
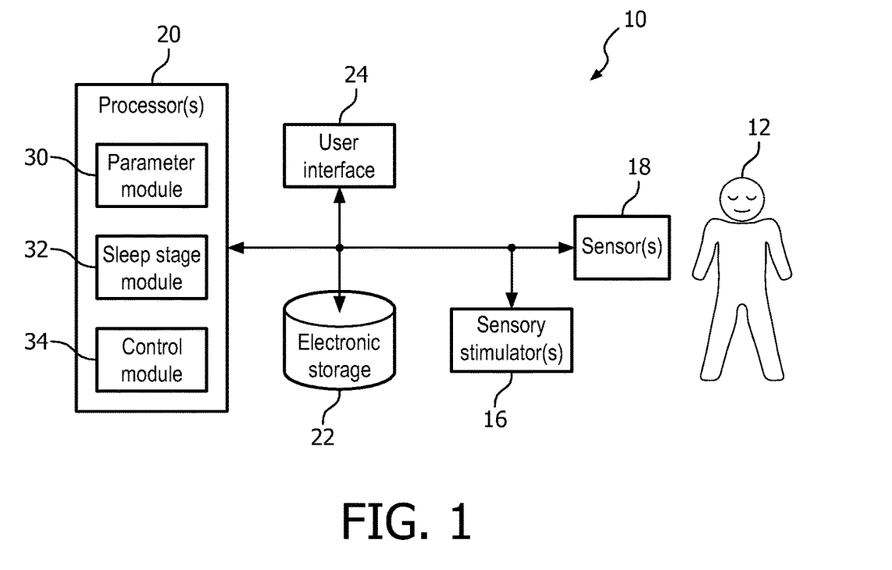
FIG. 1 is a schematic illustration of a system configured to manage a current sleep session of a subject based on output signals generated by one or more sensors that convey information related to a pulse rate and/or a blood volume of the subject during the current sleep session.

FIG. 1 is a schematic illustration of a system 10 configured to manage a current sleep session of a subject 12. In some embodiments, system 10 may comprise one or more of a sensory stimulator 16, a sensor 18, a processor 20, electronic storage 22, a user interface 24, and/or other components. System 10 is configured such that a current sleep stage of subject 12 is determined one or more times during the sleep session. The sleep stage of subject 12 is determined based on cardiac activity of subject 12. Cardiac activity may include a pulse rate of subject 12, changes in the volume of blood in the blood vessels of subject 12, and/or other cardiac activity. System 10 is configured to deliver sensory stimulation (e.g., auditory stimulation) based on output signals generated by sensor 18 that convey information related to a pulse rate of subject 12, a blood volume of subject 12, and/or other information during the current sleep session. System 10 is configured such that the delivery of sensory stimulation during sleep induces and/or enhances slow wave activity in subject 12. In some embodiments, sleep slow waves are induced, which enhances slow wave activity. The delivery of the sensory stimulation is timed to correspond to sleep stages associated with slow wave activity.

Figure 2:
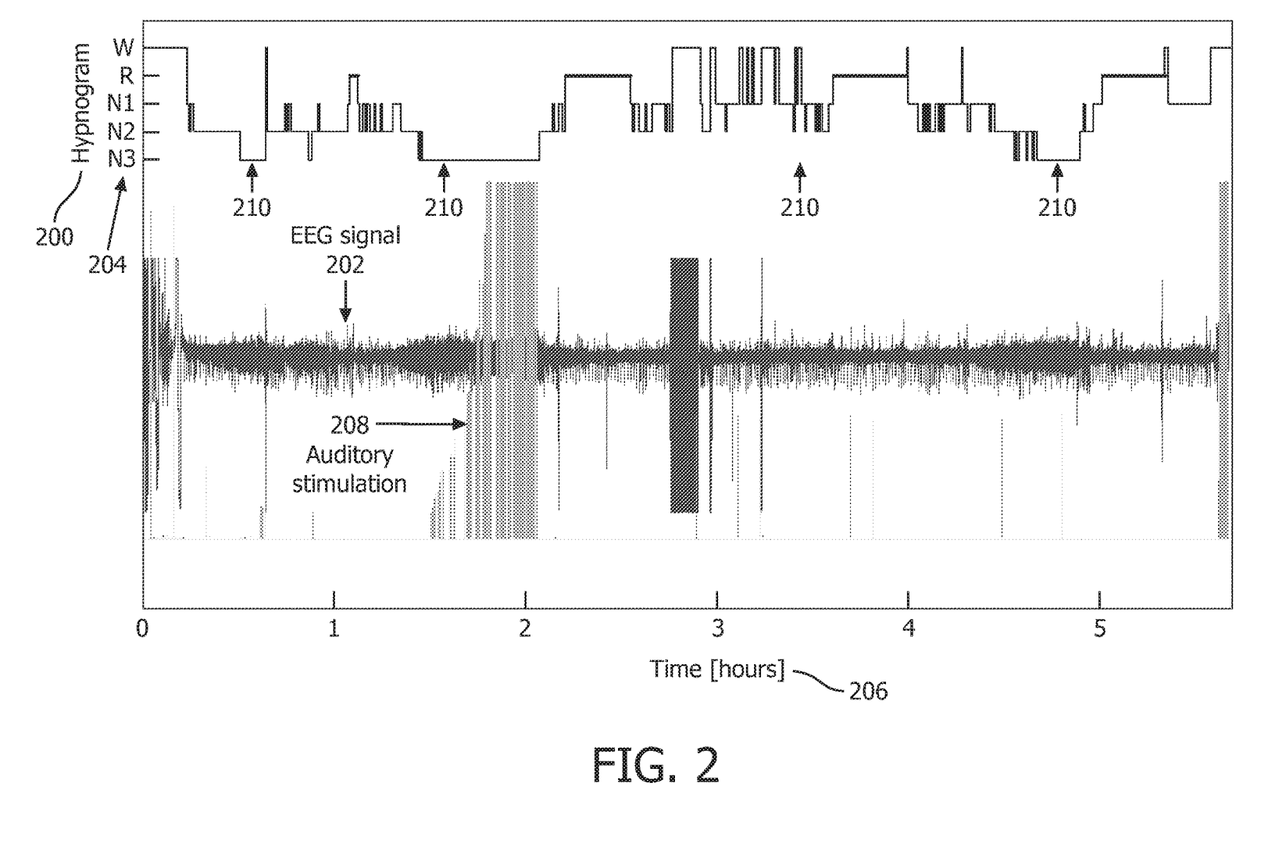
FIG. 2 illustrates a hypnogram and an EEG signal.

Slow wave sleep may be observed by way of an electroencephalogram (EEG). FIG. 2 illustrates hypnogram 200 and EEG signal 202. Hypnogram 200 illustrates sleep stage 204 variation over time 206 for a sleep session of a subject. The sleep stages may include wakefulness (W), rapid eye movement (R), and/or non-rapid eye movement stage N1, stage N2, or stage N3 sleep. In some embodiments, slow wave sleep and/or slow wave activity may correspond to stage N3 sleep. In some embodiments, stage N2 and/or stage N3 sleep may be slow wave sleep and/or correspond to slow wave activity. In the example shown in FIG. 2, auditory stimulation 208 is timed for delivery during periods of slow wave sleep 210. In some embodiments, slow waves may not be present throughout the whole N3 period, for example, but it may be significantly more likely that such slow waves are present during N3. Slow waves may also be present (although to a lesser extent) during N2, for example. The EEG signal is typically generated via a headset worn by a subject during sleep. Wearing an EEG monitoring system on the head during sleep is cumbersome and disrupts the sleep of the subject. The system described herein alleviates the need for wearing a headset during sleep.

Returning to FIG. 1, sensory stimulator 16 is configured to provide sensory stimuli to subject 12. Sensory stimulator 16 is configured to provide sensory stimuli to subject 12 prior to the current sleep session, during the current sleep session, and/or at other times. For example, sensory stimulator 16 may be configured to provide sensory stimuli to subject 12 during slow wave sleep in the current sleep session. Sensory stimulator 16 may be configured to provide sensory stimulation to subject 12 during the current sleep session to induce and/or adjust slow wave activity in subject 12. In some embodiments, sensory stimulator 16 may be configured such that adjusting includes increasing, decreasing, and/or other adjustment of slow wave activity in subject 12.

In some embodiments, sensory stimulator 16 may be configured to induce and/or adjust slow wave activity through non-invasive brain stimulation and/or other methods. Sensory stimulator 16 may be configured to induce and/or adjust slow wave activity through non-invasive brain stimulation using sensory stimuli. The sensory stimuli include odors, sounds, visual stimulation, touches, tastes, and/or other stimuli. For example, sensory stimulator 16 may be configured to induce and/or adjust slow wave activity via auditory stimulation of subject 12. Examples of sensory stimulator 16 may include one or more of a music player, a tone generator, a collection of electrodes, a unit to deliver vibratory stimulation (also known as somato-sensory stimulation), a coil generating a magnetic field to directly stimulate the brain's cortex, light generators, a fragrance dispenser, and/or other devices. In some embodiments, sensory stimulator 16, sensors 18, and/or other components of system 10 may be integrated into a single device. For example, sensory stimulator 16 may be incorporated into a wristband worn by subject 12 during sleep that also includes sensor 18. In this example embodiment, sensory stimulator 16 may be configured to deliver vibratory stimulation to the wrist of subject 12.

Sensor 18 is configured to generate output signals conveying information related to one or more of a pulse rate of subject 12, a blood volume of subject 12, movement of subject 12, and/or other characteristics of subject 12 during the current sleep session. Sensor 18 is configured to maintain the comfort of subject 12 during sleep such that sleep is not interrupted by discomfort caused by sensor 18. Sensor 18 may include an optical sensor 40 (shown in FIG. 3), a camera 50 (shown in FIG. 4), an accelerometer, and/or other sensors configured to measure the pulse rate, the blood volume, movement and/or other characteristics of subject 12. Sensor 18 may be configured to be carried (e.g., worn) by an extremity of subject 12, placed at a distance from subject 12, and/or configured in other ways. Sensor 18 may comprise one or more sensors that generate output signals conveying information related to a pulse rate of the subject, a blood volume of the subject, and/or other information indirectly. Sensor 18 may generate output signals conveying information related to movement of subject 12, respiration of subject 12, and/or other characteristics of subject 12. For example, sensor 18 may include an accelerometer such that sleep may be analyzed using actigraphy signals. The accelerometer may be integrated with sensor 18 as a single device and/or may be configured to be a stand-alone component of system 10. In some embodiments, the accelerometer may be integrated into a bracelet and/or a wrist band, for example, worn by subject 12.

Figure 3:
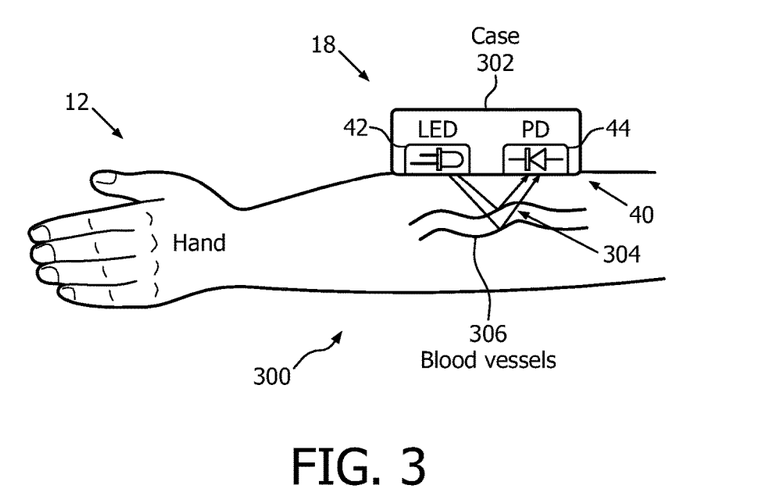
FIG. 3 illustrates an optical sensor configured to be worn on the wrist of a subject.

By way of a non-limiting example, FIG. 3 illustrates an embodiment of sensor 18 wherein sensor 18 includes optical sensor 40 and is configured to be worn on the wrist 300 of subject 12. In the example shown in FIG. 3, light source (LED) 42 and photodiode (PD) assembly 44 are housed by case 302. Light 304 from light source 42 is scattered and/or absorbed by blood in blood vessels 306. Photodiode assembly 44 generates output signals indicating an amount of light from light source 42 not absorbed by the blood in blood vessels 306 in wrist 300.

Optical Sensor 40 is configured to be carried by an extremity of subject 12. For example, FIG. 3 illustrates optical sensor 40 worn on wrist 300 of subject 12. In some embodiments, optical sensor 40 is configured such that the extremity of subject 12 includes an arm, a leg, a wrist, a finger, an ankle, a toe, and/or other extremities of subject 12. In some embodiments, optical sensor 40 may be incorporated into a bracelet and/or wrist band worn by subject 12, for example. As shown in FIG. 3, optical sensor 40 includes light source 42, photodiode assembly 44, and/or other components. In some embodiments, light source 42 and/or photodiode assembly 44 may be housed by a housing (e.g., case 302) coupled to the extremity of subject 12, coupled with a band of flexible material worn around an extremity of subject 12, removably coupled to an extremity of subject 12 via an adhesive, and/or carried by an extremity of subject 12 via other mechanisms. In some embodiments, optical sensor 40 may be incorporated into a clamp and/or other devices configured to removably couple with an extremity of subject 12. Optical sensor 40 is configured to be carried by an extremity of subject 12 such that optical sensor 40 remains in a position facing the skin of the extremity of subject 12 throughout the sleep session. In some embodiments, optical sensor 40 may be configured such that the output signals are transmitted wirelessly.

Light source 42 is configured to light an area of skin on the extremity (e.g., wrist 300) of subject 12. In some embodiments, light source 42 may be a light emitting diode (LED). The LED may emit monochromatic light. In some embodiments, the monochromatic light is green. In some embodiments, the monochromatic light is a color other than green. In some embodiments, the light is not monochromatic. At least some of the light may be scattered and/or absorbed by blood in blood vessels 306 of the area of skin. Photodiode assembly 44 is configured to generate output signals indicating an amount of light 304 from the light source not absorbed by the blood in the blood vessels in the area of skin. The amount of light 304 not absorbed is related to one or more of the pulse rate, the blood volume of the blood vessels in the area of skin, and/or other characteristics of subject 12. Output signals from photodiode 44 may indicate the blood volume and/or the pulse rate in the monitored area, for example. When the heart of subject 12 pulsates, the blood volume of the blood vessels in the skin changes and the output signals from photodiode 44 reflect this change to indicate more or less absorbed light.

Figure 4:
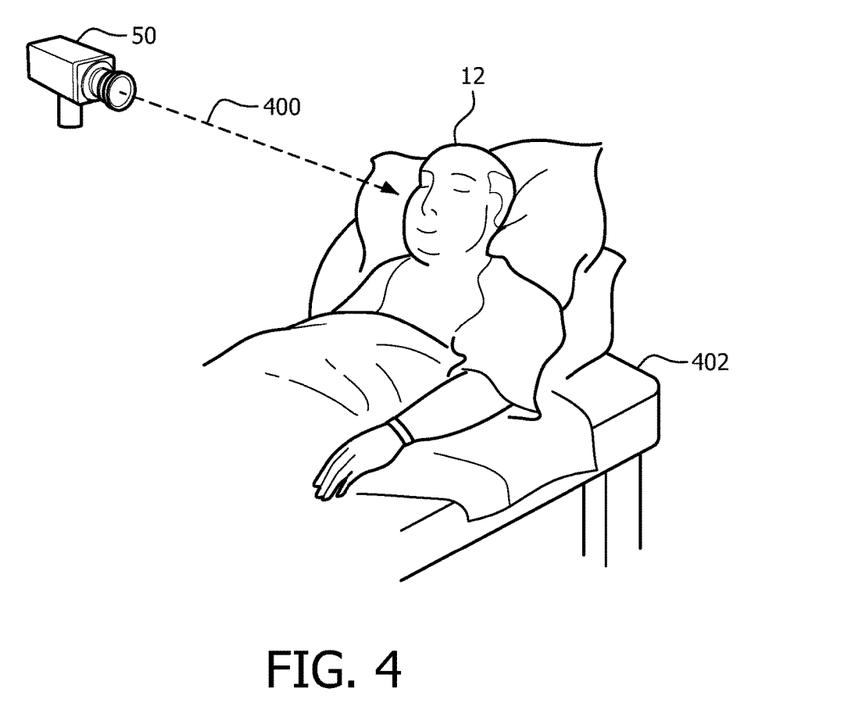
FIG. 4 illustrates a camera that is configured to be placed at a distance from a subject and directed toward an area of the skin of the body of the subject.

As shown in FIG. 4, camera 50 is configured to be placed at a distance 400 from subject 12 and directed toward an area of the skin of the body of subject 12. In some embodiments, the area of the skin of the body of subject 12 is the face of subject 12. In some embodiments, camera 50 may be directed at subject 12 while subject 12 sleeps in a bed 402, for example. Camera 50 is configured to generate output signals related to changes in the color of the skin in the area of the body of subject 12 toward which the camera is directed. The color of the skin is related to the pulse rate, the blood volume of blood vessels in the area of the body of the subject, and/or other characteristics of subject 12. Changes in the color of the skin may indicate changes in the volume of blood in the blood vessels in the monitored area, for example. In some embodiments, camera 50 may be a vital signs camera. In some embodiments, camera 50 may be a camera of a mobile device associated with subject 12 and/or other users. In some embodiments camera 50 may utilize infrared light to generate output signals related to the changes in skin color. Utilizing infrared light may decrease the likelihood that the user wakes up during the sleep session. In some embodiments, an infrared light source is placed next to the bed, which illuminates the user's body and can then enhance the signal received by the camera. In some embodiments, system 10 may be configured such that the output signals from camera 50 are transmitted wirelessly and/or via wires.

Returning to FIG. 1, although sensor 18 is described herein at a location carried by an extremity of subject 12 or located at a distance from subject 12, this is not intended to be limiting. Sensor 18 may include one or more of the different types of sensors (e.g., optical sensors, camera sensors) disposed in a plurality of locations. For example, multiple sensors 18 may be disposed on multiple limbs of subject 12. An optical sensor may be disposed on an extremity of subject 12 while a camera is disposed at a distance from subject 12. Multiple cameras may be disposed at multiple distances from subject 12.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program modules. The one or more computer program modules may comprise one or more of a parameter module 30, a sleep stage module 32, a control module 34, and/or other modules. Processor 20 may be configured to execute modules 30, 32, and/or 34 by software; hardware; firmware; some combination of software, hardware, and/or firmware; and/or other mechanisms for configuring processing capabilities on processor 20.

It should be appreciated that although modules 30, 32, and 34 are illustrated in FIG. 1 as being co-located within a single processing unit, in embodiments in which processor 20 comprises multiple processing units, one or more of modules 30, 32, and/or 34 may be located remotely from the other modules. The description of the functionality provided by the different modules 30, 32, and/or 34 described below is for illustrative purposes, and is not intended to be limiting, as any of modules 30, 32, and/or 34 may provide more or less functionality than is described. For example, one or more of modules 30, 32, and/or 34 may be eliminated, and some or all of its functionality may be provided by other modules 30, 32, and/or 34. As another example, processor 20 may be configured to execute one or more additional modules that may perform some or all of the functionality attributed below to one of modules 30, 32, and/or 34.

Parameter module 30 is configured to determine one or more cardiac activity parameters based on the output signals from sensors 18. The one or more cardiac activity parameters include a pulse rate metric, a blood volume metric, and/or other parameters. The pulse rate metric may be related to heart rate variability (HRV), and/or other pulse rate metrics. Heart rate variability is defined as the variation in the time interval between heartbeats. The blood volume metric may be related to low frequency changes in blood volume in about the 0.04-0.30 Hz range, for example, and/or other blood volume metrics. The pulse rate metric, the blood volume metric, and/or other parameters may be related to the current sleep stage of subject 12 during the current sleep session. In some embodiments, parameter module 30 may be configured to determine the pulse rate metric, the blood volume metric, and/or other parameters directly from the output signals of sensor 18. In some embodiments, parameter module 30 is configured to determine the pulse rate metric and/or the blood volume metric from previously determined parameters. For example, parameter module 30 may be configured to determine the changes in a blood volume of an area of skin based on the output signals from sensors 18. Parameter module 30 may determine a pulse rate based on the frequency, the amplitude, and/or other characteristics of the changes in the blood volume of the area of skin over time. As another example, parameter module 30 may be configured to determine the changes in color of an area of skin of subject 12 based on the output signals from sensors 18. Parameter module 30 may determine a pulse rate based on the frequency, the colors, and/or other characteristics of the changes in the skin properties over time. In some embodiments, parameter module 30 is configured to determine an arousal metric indicating a level of wakefulness in subject 12 based on the output signals of sensor 18. The arousal metric may be determined based on movement of subject 12, for example. Movement of subject 12 may be determined based on high frequency noise in the cardiac signals from sensors 18, movement of subject 12 determined via camera 50, movement of subject 12 determined via the accelerometer, and or based on other information.

Figure 5:
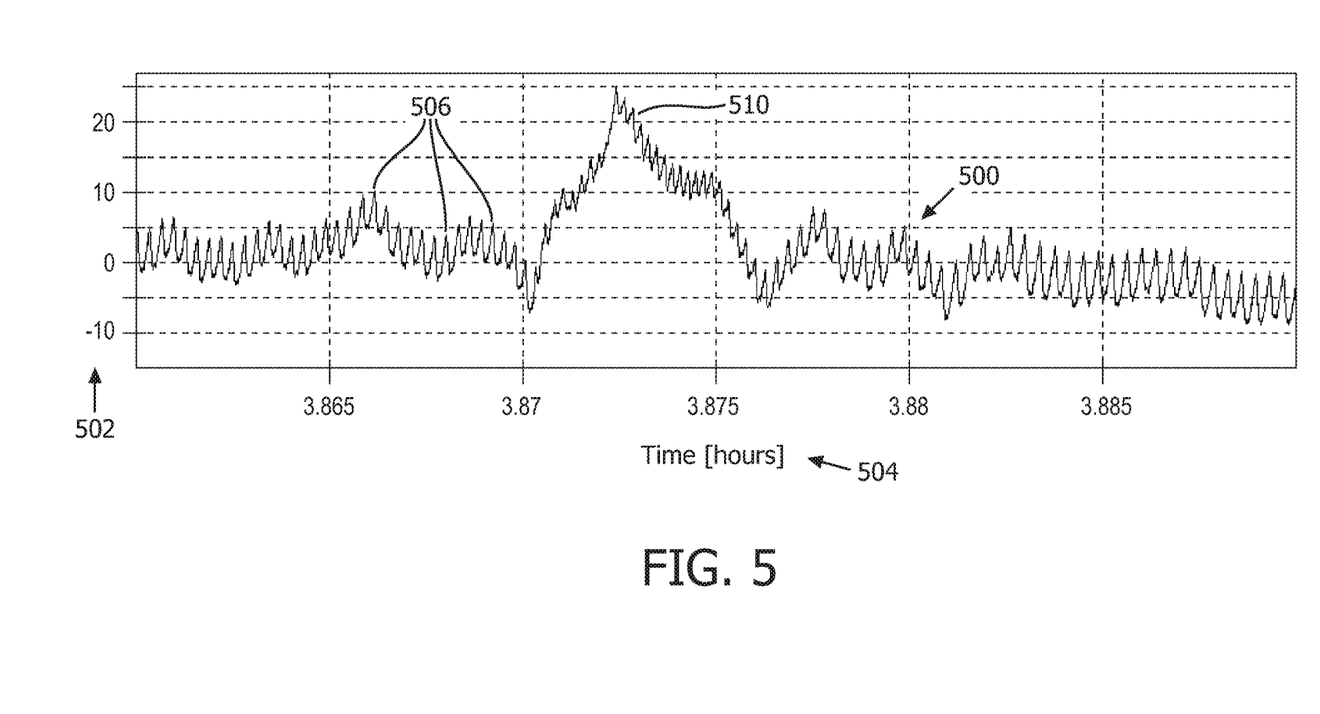
FIG. 5 illustrates high frequency variation that corresponds to the pulse rate of a subject.

FIG. 5 illustrates an example of an output signal 500 from sensor 18 (shown in FIG. 1). The characteristics (e.g., frequency, amplitude, baseline variations, peak to peak time intervals, etc.) of output signal 500 may be used by parameter module 30 (shown in FIG. 1) to determine the one or more cardiac activity parameters and/or other information during the current sleep session. Output signal 500 may illustrate a signal representing changes in blood volume, for example, generated by optical sensor 40 (shown in FIG. 3), camera 50 (shown in FIG. 4), and/or other sensors. The signal strength 502 of output signal 500 varies over time 504. Peaks 506 in signal 500 appear approximately every second in this example and represent heart beats of a subject (e.g., subject 12). Parameter module 30 may determine heart rate variability, for example, based on peaks 506.

Returning to FIG. 1, sleep stage module 32 is configured to determine the current sleep stage of subject 12 based on the determined cardiac activity parameters, the output signals from sensors 18, and/or other information. As described above, the current sleep stage of subject 12 may correspond to one or more of wakefulness, REM sleep, stage N1, stage N2, and/or stage N3 sleep. Sleep stage module 32 is configured to determine whether subject 12 is presently in slow wave sleep. In some embodiments, slow wave sleep and/or slow wave activity may correspond to stage N3 sleep. In some embodiments, stage N2 and/or stage N3 sleep may be slow wave sleep and/or correspond to slow wave activity.

In some embodiments, sleep stage module 32 is configured to determine the current sleep stage of the subject based on the pulse rate metric (e.g., the heart rate variability). For example, as the subject progresses into deeper and deeper stages of sleep, the pulse rate of the subject and/or the pulse rate metric may show a corresponding decrease. Sleep stage module 32 may be configured to determine the current sleep stage based on the decrease in the pulse rate metric.

In some embodiments, sleep stage module 32 is configured to determine the current sleep stage of the subject based on the blood volume metric. For example, low frequency changes in blood volume (in about the range 0.04-0.30 Hz for example) are related to the activity of the parasympathetic nervous system in subject 12. The parasympathetic nervous system is responsible for regulating activities that occur when the body is at rest. The behavior of the parasympathetic nervous system during sleep is different than the behavior of the parasympathetic nervous system during wakefulness because the level of consciousness during sleep interferes less with ongoing processes in the brain. During sleep, the low frequency oscillations decrease in intensity compared to the wakeful state such that the intensity of the low frequency oscillations is lowest during stage N3 sleep. Sleep stage module 32 may be configured to determine the current sleep stage based on the decrease in the intensity of the low frequency oscillations.

For example, FIG. 5 illustrates high frequency peak 506 to peak 506 oscillation in output signal 500 strength at a frequency of about 1 Hz that corresponds to the pulse rate of a subject (e.g., subject 12). A low frequency oscillation in the range 0.04-0.3 Hz indicated by peak 510 is superimposed on the high frequency oscillation (subsequent peaks 510 are not shown in FIG. 5). The low frequency oscillation is related to the activity of the parasympathetic nervous system. Sleep stage module 32 (FIG. 1) may determine whether the subject is presently in slow wave sleep based at least in part on differences in the intensities of the low frequency oscillations for individual sleep stages.

Figure 6A:
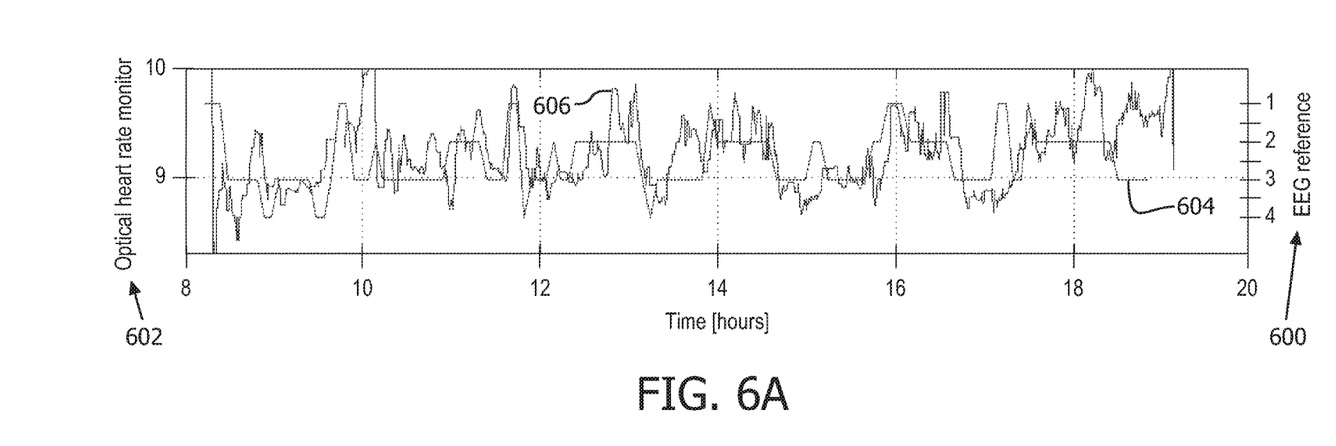
FIG. 6A illustrates an example of a comparison between sleep stages determined from an EEG and the output signals from a sensor in the 0.04-0.30 Hz range.

FIG. 6A illustrates a comparison between sleep stages determined from an EEG 600 and a blood volume metric 602 (e.g., based on the output signals of optical sensor 40 in the 0.04-0.30 Hz range) for a subject. Sleep stage variation over time 604 determined from EEG 600 and variation of the blood volume metric over time 606 generally correlate with each other. The general correlation of sleep stage variation over time 604 and the blood volume metric over time 606 indicates that low frequency oscillations of the blood volume are related to the sleep stage in a subject such that sleep stage module 32 (shown in FIG. 1) may determine the current sleep stage of subject 12 based on the determined blood volume metric and/or the output signals from sensors 18.

Figure 6B:
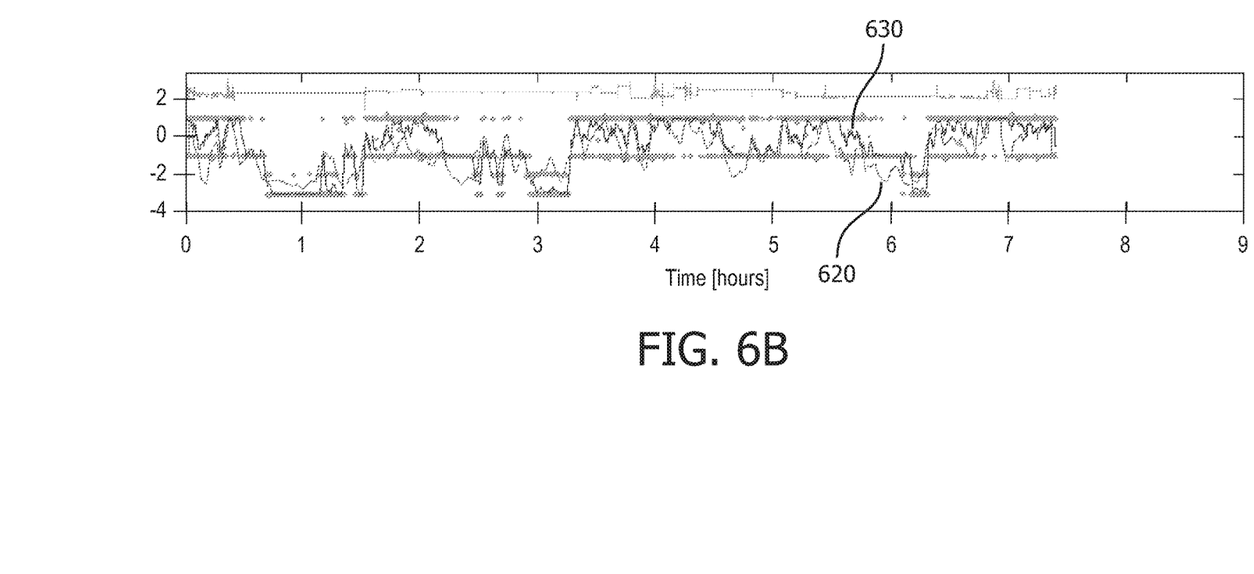
FIG. 6B illustrates that heart rate variability over time generally correlates with sleep stage variation over time such that a sleep stage module may determine the current sleep stage of a subject based on the determined heart rate variability.

Similarly, FIG. 6B illustrates that heart rate variability (the pulse rate metric) 620 over time generally correlates with sleep stage variation 630 over time such that sleep stage module 32 (shown in FIG. 1) may determine the current sleep stage of subject 12 based on the determined heart rate variability. Heart rate variability over time 620 may be determined by parameter module 30. Sleep stage variation over time 630 may be determined via an EEG by using, for example, the heart rate variability information conveyed by the ECG signals.

Control module 34 is configured to control the one or more sensory stimulators to provide the sensory stimuli to the subject to induce and/or adjust slow wave activity in the subject while the subject is determined to be in slow wave sleep (e.g., stage N3). In some embodiments, adjusting slow wave activity may include enhancing slow wave activity. In some embodiments, the one or more sensory stimulators are controlled to provide sensory stimuli to the subject to induce sleep slow waves. In some embodiments, the manifestation of induced sleep slow waves may be measured via slow wave activity.

In some embodiments, control module 34 may determine timing for delivery of sensory stimulation. In some embodiments, the timing for delivery of sensory stimulation may correspond to the determination that subject 12 is presently in slow wave sleep. For example, control module 34 may be configured to determine timing for delivery of sensory stimulation such that auditory stimulation is delivered to subject 12 a predetermined amount of time after sleep stage module 32 determines that subject 12 is presently in sleep stage N3. Control module 34 may be configured to determine a timing for delivery of sensory stimulation such that the determined timing corresponds to sleep stages associated with slow wave activity because the likelihood for slow-wave induction, and/or adjustment during the specific sleep stage may be comparatively higher than in other sleep stages, the user may be less likely to be awakened by the sensory stimuli, and/or for other reasons. In some embodiments, control module 34 is configured to control sensory stimulator 16 to cease providing the sensory stimuli to subject 12 responsive to the arousal metric determined by parameter module 30 indicating that subject 12 is waking up.

In some embodiments, control module 34 may be configured to control sensory stimulator 16 to adjust slow wave activity in subject 12 during the current sleep session. Adjusting slow wave activity in subject 12 while subject 12 is asleep during the current sleep session may include controlling sensory stimulator 16 to increase and/or decrease slow wave activity in subject 12 during sleep. In some embodiments, control module 34 may control sensory stimulator 16 to provide the sensory stimulation during the current sleep session such that the sensory stimulation does not wake subject 12. For example, control module 34 may control sensory stimulator 16 to provide the sensory stimulation at a low intensity level.

In some embodiments, control module 34 may cause information related to the current sleep session of subject 12 to be stored in electronic storage 22. Information related to the current sleep session may include information related to a sleep pressure, slow wave activity induction and/or adjustments, the intensity level of the stimulation, a sleep stage, timing information, information related to the one or more cardiac activity parameters, and/or other information.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, the cardiac activity parameters may be displayed to a caregiver via user interface 24. As another example, user interface 24 may be configured to receive entry and/or selection of sensor 18 configuration information. The configuration information may allow a user to customize the operation of sensor 18 and/or other aspects of system 10.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16, sensory stimulator 16, and/or other components of system 10. In some embodiments, user interface 24 may include camera 50, for example.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
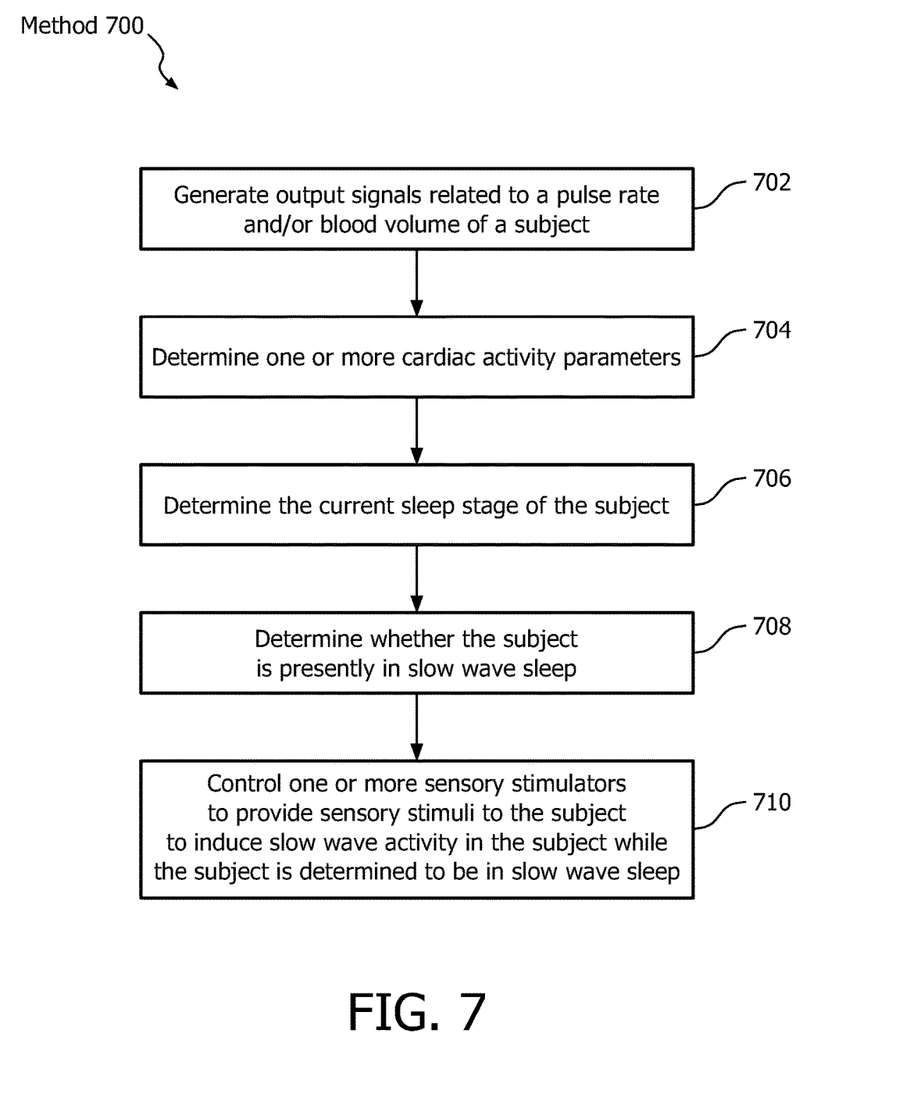
FIG. 7 illustrates a method for managing a current sleep session of a subject with a management system.

FIG. 7 illustrates a method 700 for managing a current sleep session of a subject with a management system. The system comprises one or more sensory stimulators, one or more sensors, and one or more processors configured to execute computer program modules. The computer program modules comprise a parameter module, a sleep stage module, and a control module. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to one or more of a pulse rate of the subject, a blood volume of the subject, and/or other information is generated during the current sleep session. In some embodiments, operation 702 is performed by one or more sensors the same as or similar to sensors 18 (shown in FIG. 1 and described herein).

At an operation 704, one or more cardiac activity parameters are determined based on the output signals. The one or more cardiac activity parameters include one or more of a pulse rate metric, a blood volume metric, and/or other parameters. The pulse rate metric and the blood volume metric are related to a current sleep stage of the subject during the current sleep session. In some embodiments, operation 704 is performed by a parameter module the same as or similar to parameter module 30 (shown in FIG. 1 and described herein).

At an operation 706, the current sleep stage of the subject is determined based on the determined parameters. In some embodiments, operation 706 is performed by a sleep stage module the same as or similar to sleep stage module 32 (shown in FIG. 1 and described herein).

At an operation 708, whether the subject is presently in slow wave sleep is determined. In some embodiments, operation 708 is performed by a sleep stage module the same as or similar to sleep stage module 32 (shown in FIG. 1 and described herein).

At an operation 710, the one or more sensory stimulators are controlled to provide sensory stimuli to the subject to induce slow wave activity in the subject while the subject is determined to be in slow wave sleep. In some embodiments, operation 710 is performed by a control module the same as or similar to control module 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to manage a current sleep session of a subject, the system comprising:
   one or more sensory stimulators configured to provide sensory stimuli to the subject;
   one or more sensors configured to generate output signals conveying information related to a blood volume of the subject during the current sleep session, the one or more sensors including an optical sensor configured to be carried by an extremity of the subject, the optical sensor including:
      a light source configured to light an area of skin on the extremity of the subject, wherein at least some of the light is absorbed by blood in blood vessels of the area of skin; and
      a photodiode assembly configured to generate output signals indicating an amount of light from the light source not absorbed by the blood in the blood vessels in the area of skin, the amount of light not absorbed being related to blood volume of the blood vessels in the area of skin; and
   one or more processors configured to execute computer program modules, the computer program modules comprising:
      a parameter module configured to determine a blood volume metric, the blood volume metric being related to a current sleep stage of the subject during the current sleep session;
      a sleep stage module configured to determine the current sleep stage of the subject based on the blood volume metric, the sleep stage module configured to determine whether the subject is presently in slow wave sleep; and
      a control module configured to control the one or more sensory stimulators to provide the sensory stimuli to enhance slow wave activity in the subject while the subject is determined to be in slow wave sleep.

2. The system of claim 1, wherein the optical sensor is configured such that the extremity of the subject includes an arm, a leg, a wrist, a finger, an ankle, or a toe of the subject.

3. The system of claim 1, wherein the one or more sensors include a camera placed at a distance from the subject and directed toward an area of the body of the subject, the camera configured to generate output signals related to changes in a color of the skin in the area of the body of the subject, the color of the skin being related to one or more of a pulse rate or a blood volume of blood vessels in the area of the body of the subject that the camera is directed towards.

4. The system of claim 1, wherein the sleep stage module is configured such that slow wave sleep corresponds to a sleep stage N3.

5. The system of claim 1, wherein the one or more sensors are further configured to generate output signals conveying information related to arousals of the subject, the arousals being related to wakefulness in the subject,
wherein the parameter module is further configured to determine an arousal metric based on the output signals conveying information related to arousals of the subject, and
wherein, responsive to the arousal metric indicating that the subject is waking up, the control module is configured to control the one or more sensory stimulators to cease providing the sensory stimuli to the subject.

6. A method for providing sensory stimulation to a subject with a management system, the system comprising one or more sensory stimulators, one or more sensors, and one or more processors configured to execute computer program modules, the computer program modules comprising a parameter module, a sleep stage module, and a control module, the method comprising:
generating output signals conveying information related to a blood volume of the subject during the current sleep session with the one or more sensors, wherein the one or more sensors include an optical sensor configured to be carried by an extremity of the subject, the optical sensor including a light source and a photodiode assembly;
lighting, with the light source, an area of skin on the extremity of the subject, wherein at least some of the light is absorbed by blood in blood vessels of the area of skin; and
generating, with the photodiode assembly, output signals indicating an amount of light from the light source not absorbed by the blood in the blood vessels in the area of skin, the amount of light not absorbed being related to blood volume of the blood vessels in the area of skin;
determining, with the parameter module, a blood volume metric, the blood volume metric being related to a current sleep stage of the subject during the current sleep session;
determining, with the sleep stage module, the current sleep stage of the subject based on the blood volume metric;
determining, with the sleep stage module, whether the subject is presently in slow wave sleep; and
controlling, with the control module, the one or more sensory stimulators to provide sensory stimuli to the subject to induce slow wave activity in the subject while the subject is determined to be in slow wave sleep.

7. The method of claim 6, wherein the extremity of the subject includes an arm, a leg, a wrist, a finger, an ankle, or a toe of the subject.

8. The method of claim 6, wherein the one or more sensors include a camera placed at a distance from the subject and directed toward an area of the body of the subject, the method further comprising generating, with the camera, output signals related to changes in a color of the skin in the area of the body of the subject, the color of the skin being related to one or more of a pulse rate or the blood volume of blood vessels in the area of the body of the subject that the camera is directed towards.

9. The method of claim 6, wherein slow wave sleep corresponds to a sleep stage N3.

10. The method of claim 6, further comprising generating output signals conveying information related to arousals of the subject, the arousals being related to wakefulness in the subject,
determining an arousal metric based on the output signals conveying information related to arousals of the subject, and
responsive to the arousal metric indicating that the subject is waking up, controlling the one or more sensory stimulators to cease providing the sensory stimuli to the subject.

11. A system configured to manage a current sleep session of a subject, the system comprising:
means for providing sensory stimuli to the subject;
means for generating output signals conveying information related to a blood volume of the subject during the current sleep session the means for generating output signals including optical sensing means configured to be carried by an extremity of the subject, the optical sensing means including:
means for lighting an area of skin on the extremity of the subject, wherein at least some of the light is absorbed by blood in blood vessels of the area of skin; and
means for generating output signals indicating an amount of light from the light source not absorbed by the blood in the blood vessels in the area of skin, the amount of light not absorbed being related to blood volume of the blood vessels in the area of skin;
means for determining a blood volume metric, the blood volume metric being related to a current sleep stage of the subject during the current sleep session;
means for determining the current sleep stage of the subject based on the blood volume metric, the means for determining the current sleep stage configured to determine whether the subject is presently in slow wave sleep; and
means for controlling the means for providing sensory stimuli to provide the sensory stimuli to the subject to induce slow wave activity in the subject while the subject is determined to be in slow wave sleep.

12. The system of claim 11, wherein the optical sensing means are configured such that the extremity of the subject includes an arm, a leg, a wrist, a finger, an ankle, or a toe of the subject.

13. The system of claim 11, wherein the means for generating output signals include means for generating output signals related to changes in a color of the skin in an area of the body of the subject, the color of the skin being related to one or more of a pulse rate or the blood volume of blood vessels in the area of the body of the subject, the means for generating output signals related to changes in skin color being placed at a distance from the subject and directed toward the area of the body of the subject that the camera is directed towards.

14. The system of claim 11, wherein the means for determining the current sleep stage is configured such that slow wave sleep corresponds to a sleep stage N3.

15. The system of claim 11, wherein the means for generating output signals are further configured to generate output signals conveying information related to arousals of the subject, the arousals being related to wakefulness in the subject,
wherein the means for determining blood volume metric is further configured to determine an arousal metric based on the output signals conveying information related to arousals of the subject, and wherein, responsive to the arousal metric indicating that the subject is waking up, the means for controlling the means for providing sensory stimuli is configured to control the means for providing sensory stimuli to cease providing the sensory stimuli to the subject.

* * * * *